(12) United States Patent
Tsuji

(10) Patent No.: US 10,709,402 B2
(45) Date of Patent: Jul. 14, 2020

(54) RADIOGRAPHY SYSTEM, RADIOGRAPHY METHOD, RADIOGRAPHY PROGRAM, AND DERIVATION APPARATUS

(71) Applicant: FUJIFILM CORPORATION, Minato-ku, Tokyo (JP)

(72) Inventor: Tetsuya Tsuji, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 94 days.

(21) Appl. No.: 15/980,754

(22) Filed: May 16, 2018

(65) Prior Publication Data
US 2018/0333122 A1    Nov. 22, 2018

(30) Foreign Application Priority Data

May 18, 2017 (JP) .................. 2017-099103

(51) Int. Cl.
*G01T 1/20* (2006.01)
*A61B 6/00* (2006.01)

(52) U.S. Cl.
CPC ............ *A61B 6/505* (2013.01); *A61B 6/4233* (2013.01); *A61B 6/4241* (2013.01); *A61B 6/4266* (2013.01); *A61B 6/482* (2013.01); *A61B 6/5205* (2013.01); *G01T 1/20* (2013.01)

(58) Field of Classification Search
CPC ..... A61B 6/505; A61B 6/4266; A61B 6/4241; A61B 6/5205; A61B 6/4233; A61B 6/4208; G01T 1/2018
See application file for complete search history.

(56) References Cited

U.S. PATENT DOCUMENTS

| 6,031,892 A * | 2/2000 | Karellas ................... A61B 6/06 250/370.09 |
| 2002/0067799 A1* | 6/2002 | Mitchell ............... A61B 6/4216 378/62 |
| 2004/0077088 A1* | 4/2004 | Charles, Jr. ............ A61B 6/032 435/455 |

FOREIGN PATENT DOCUMENTS

JP          H04-297234       10/1992

* cited by examiner

Primary Examiner — David P Porta
Assistant Examiner — Fani Boosalis
(74) *Attorney, Agent, or Firm* — SOLARIS Intellectual Property Group, PLLC

(57) ABSTRACT

A radiography system includes a radiography apparatus including two radiation detectors and a console that corrects a ratio of pixel values in a region, which corresponds to a soft tissue of a subject and is a corresponding region of radiographic images generated by the two radiation detectors irradiated with radiations having different energy levels, on the basis of correction data corresponding to a body thickness, and derives the bone density of the subject on the basis of a difference between a ratio of pixel values in a region corresponding to a bone tissue of the subject and the corrected ratio of the pixel values.

7 Claims, 13 Drawing Sheets

| BODY THICKNESS [cm] | PIXEL VALUE |
|---|---|
| 10 | 1804 |
| 15 | 1724 |
| 20 | 1656 |
| 25 | 1604 |
| 30 | 1569 |

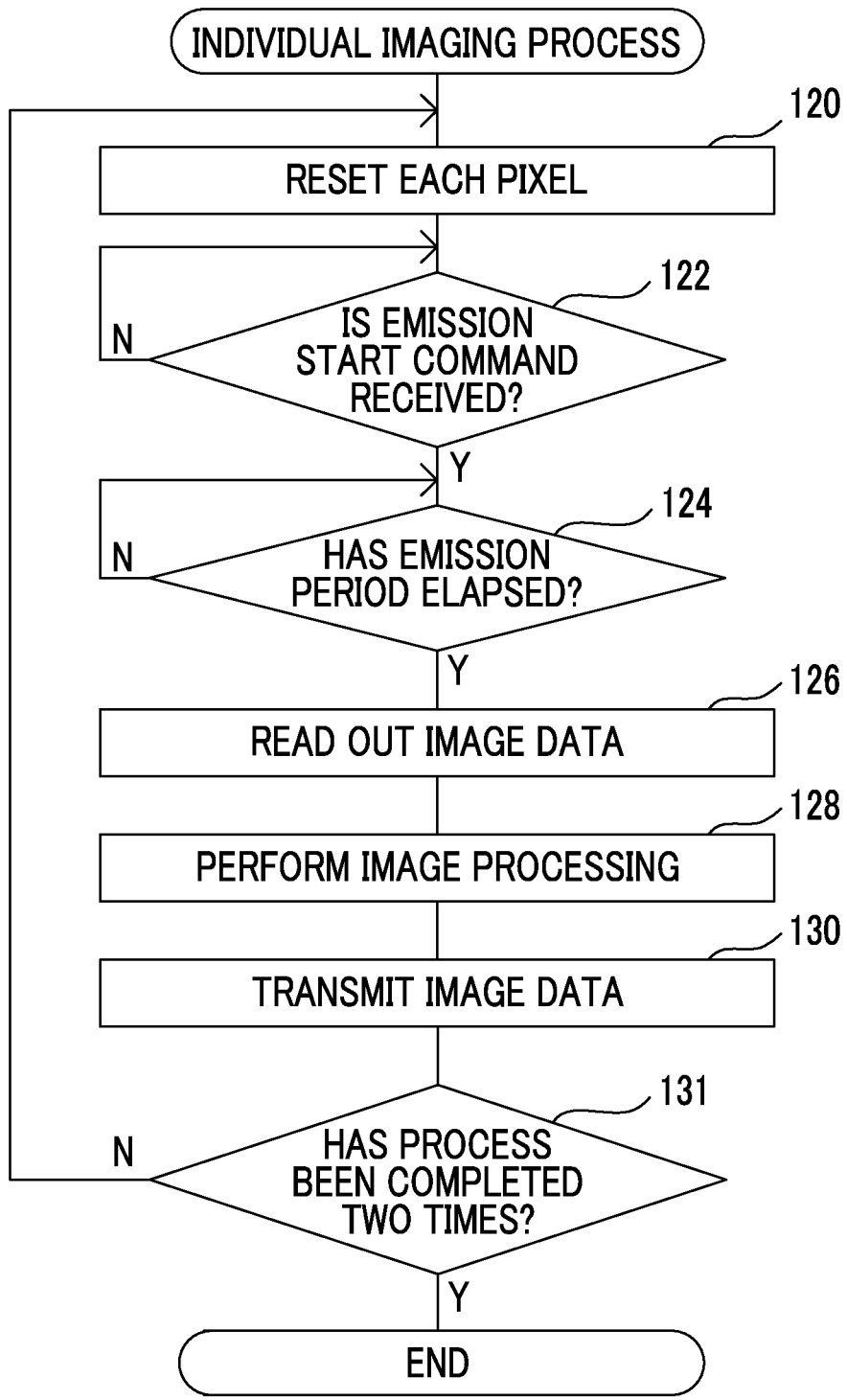

RADIOGRAPHY SYSTEM, RADIOGRAPHY METHOD, RADIOGRAPHY PROGRAM, AND DERIVATION APPARATUS

CROSS-REFERENCE TO RELATED APPLICATION

This application claims priority under 35 USC 119 from Japanese Patent Application No. 2017-099103 filed on May 18, 2017, the disclosure of which is incorporated by reference herein in its entirety.

BACKGROUND OF THE INVENTION

1. Field of the Invention

The present disclosure relates to a radiography system, a radiography method, a radiography program, and a derivation apparatus.

2. Description of the Related Art

In the related art, a technique has been proposed which performs an energy subtraction process, using two radiographic images generated by irradiating two accumulative phosphor sheets with radiations having different energy levels (see JP1992-297234A (JP-H04-297234A)). In this technique, the bone mineral content of a subject is derived using the images obtained by the energy subtraction process.

SUMMARY OF THE INVENTION

The results of thorough examinations by the inventors of the invention prove that, in a case in which the bone mineral content and bone density of a subject are derived using each radiographic image generated by radiation detectors irradiated with radiations having different energy levels, the body thickness of the subject affects the accuracy of the derived bone mineral content and bone density.

That is, even in a case in which the bone mineral content and bone density of the subject are the same, the quality and amount of radiation absorbed in the body of the subject vary depending on the body thickness of the subject. Therefore, in some cases, different values are derived as the bone mineral content and the bone density.

However, in the technique disclosed in JP1992-297234A (JP-H04-297234A), the body thickness of the subject is not considered.

The present disclosure has been made in view of the above-mentioned problems and an object of the present disclosure is to provide a technique that can accurately derive at least one of bone density or bone mineral content of a subject, using each radiographic image generated by irradiation with radiations having different energy levels.

In order to achieve the object, a radiography system according to the present disclosure comprises: a radiography apparatus including two radiation detectors in which a plurality of pixels, each of which includes a conversion element that generates a larger amount of charge as it is irradiated with a larger amount of radiation, are two-dimensionally arranged and which are arranged in a direction in which the radiation is emitted; a correction unit that corrects a ratio of pixel values in a region, which corresponds to a soft tissue of a subject and is a corresponding region of radiographic images generated by the two radiation detectors irradiated with radiations having different energy levels, on the basis of correction data corresponding to a body thickness; and a derivation unit that derives at least one of bone density or bone mineral content of the subject on the basis of a difference between a ratio of pixel values in a region, which corresponds to a bone tissue of the subject and is a corresponding region of the radiographic images, and the ratio of the pixel values corrected by the correction unit.

In order to achieve the object, a radiography system according to the present disclosure comprises: a radiography apparatus including a single radiation detector in which a plurality of pixels, each of which includes a conversion element that generates a larger amount of charge as it is irradiated with a larger amount of radiation, are two-dimensionally arranged; a correction unit that corrects a ratio of pixel values in a region, which corresponds to a soft tissue of a subject and is a corresponding region of radiographic images generated by the radiation detector irradiated with radiations having different energy levels, on the basis of correction data corresponding to a body thickness; and a derivation unit that derives at least one of bone density or bone mineral content of the subject on the basis of a difference between a ratio of pixel values in a region, which corresponds to a bone tissue of the subject and is a corresponding region of the radiographic images, and the ratio of the pixel values corrected by the correction unit.

In the radiography system according to the present disclosure, the correction data may include a correction value for each pixel. The correction value of a region corresponding to the soft tissue may become smaller as the pixel becomes further away from a region corresponding to the bone tissue increases. A difference between the correction value of the region corresponding to the soft tissue and the correction value of the region corresponding to the bone tissue may increase as the body thickness increases.

The radiography system according to the present disclosure may further comprise: an estimation unit that estimates the body thickness of the subject on the basis of correspondence relationship information in which the body thickness is associated with the ratio of the pixel values in the region corresponding to the soft tissue.

In the radiography system according to the present disclosure, each of the two radiation detectors may comprise a light emitting layer that is irradiated with radiation and emits light. The plurality of pixels of each of the two radiation detectors may receive the light, generate the charge, and accumulate the charge. The light emitting layer of one of the two radiation detectors which is provided on an incident side of the radiation may include CsI and the light emitting layer of the other radiation detector may include GOS.

In order to achieve the object, the present disclosure provides a radiography method that is performed by a radiography apparatus including two radiation detectors in which a plurality of pixels, each of which includes a conversion element that generates a larger amount of charge as it is irradiated with a larger amount of radiation, are two-dimensionally arranged and which are arranged in a direction in which the radiation is emitted. The radiography method comprises: correcting a ratio of pixel values in a region, which corresponds to a soft tissue of a subject and is a corresponding region of radiographic images generated by the two radiation detectors irradiated with radiations having different energy levels, on the basis of correction data corresponding to a body thickness; and deriving at least one of bone density or bone mineral content of the subject on the basis of a difference between a ratio of pixel values in a region, which corresponds to a bone tissue of the subject and is a corresponding region of the radiographic images, and the corrected ratio of the pixel values.

In order to achieve the object, the present disclosure provides a radiography method that is performed by a radiography apparatus including a single radiation detector in which a plurality of pixels, each of which includes a conversion element that generates a larger amount of charge as it is irradiated with a larger amount of radiation, are two-dimensionally arranged. The radiography method comprises: correcting a ratio of pixel values in a region, which corresponds to a soft tissue of a subject and is a corresponding region of radiographic images generated by the radiation detector irradiated with radiations having different energy levels, on the basis of correction data corresponding to a body thickness; and deriving at least one of bone density or bone mineral content of the subject on the basis of a difference between a ratio of pixel values in a region, which corresponds to a bone tissue of the subject and is a corresponding region of the radiographic images, and the corrected ratio of the pixel values.

In order to achieve the object, the present disclosure provides a radiography program that causes a computer controlling a radiography apparatus including two radiation detectors in which a plurality of pixels, each of which includes a conversion element that generates a larger amount of charge as it is irradiated with a larger amount of radiation, are two-dimensionally arranged and which are arranged in a direction in which the radiation is emitted to perform: correcting a ratio of pixel values in a region, which corresponds to a soft tissue of a subject and is a corresponding region of radiographic images generated by the two radiation detectors irradiated with radiations having different energy levels, on the basis of correction data corresponding to a body thickness; and deriving at least one of bone density or bone mineral content of the subject on the basis of a difference between a ratio of pixel values in a region, which corresponds to a bone tissue of the subject and is a corresponding region of the radiographic images, and the corrected ratio of the pixel values.

In order to achieve the object, the present disclosure provides a radiography program that causes a computer controlling a radiography apparatus including a single radiation detector in which a plurality of pixels, each of which includes a conversion element that generates a larger amount of charge as it is irradiated with a larger amount of radiation, are two-dimensionally arranged to perform: correcting a ratio of pixel values in a region, which corresponds to a soft tissue of a subject and is a corresponding region of radiographic images generated by the radiation detector irradiated with radiations having different energy levels, on the basis of correction data corresponding to a body thickness; and deriving at least one of bone density or bone mineral content of the subject on the basis of a difference between a ratio of pixel values in a region, which corresponds to a bone tissue of the subject and is a corresponding region of the radiographic images, and the corrected ratio of the pixel values.

In order to achieve the object, the present disclosure provides a derivation apparatus comprising: a correction unit that corrects, on the basis of correction data corresponding to a body thickness, a ratio of pixel values in a region which corresponds to a soft tissue of a subject and is a corresponding region of radiographic images generated by two radiation detectors, which are provided in a radiography apparatus so as to be arranged in a direction in which radiation is emitted and include a plurality of pixels each of which includes a conversion element that generates a larger amount of charge as it is irradiated with a larger amount of radiation and which are two-dimensionally arranged, in a case in which the radiography apparatus is irradiated with radiations having different energy levels; and a derivation unit that derives at least one of bone density or bone mineral content of the subject on the basis of a difference between a ratio of pixel values in a region, which corresponds to a bone tissue of the subject and is a corresponding region of the radiographic images, and the ratio of the pixel values corrected by the correction unit.

In order to achieve the object, the present disclosure provides a derivation apparatus comprising: a correction unit that corrects, on the basis of correction data corresponding to a body thickness, a ratio of pixel values in a region which corresponds to a soft tissue of a subject and is a corresponding region of radiographic images generated by a single radiation detector, which is provided in a radiography apparatus and includes a plurality of pixels each of which includes a conversion element that generates a larger amount of charge as it is irradiated with a larger amount of radiation and which are two-dimensionally arranged, in a case in which the radiography apparatus is irradiated with radiations having different energy levels; and a derivation unit that derives at least one of bone density or bone mineral content of the subject on the basis of a difference between a ratio of pixel values in a region, which corresponds to a bone tissue of the subject and is a corresponding region of the radiographic images, and the ratio of the pixel values corrected by the correction unit.

According to the present disclosure, it is possible to accurately derive at least one of the bone density or the bone mineral content of the subject, using each radiographic image generated by irradiation with radiations having different energy levels.

BRIEF DESCRIPTION OF THE DRAWINGS

FIG. 22 is a flowchart illustrating the process flow of an individual imaging processing program according to the second embodiment.

DESCRIPTION OF THE PREFERRED EMBODIMENTS

Hereinafter, embodiments of the present disclosure will be described in detail with reference to the drawings.

First Embodiment

Figure 1:
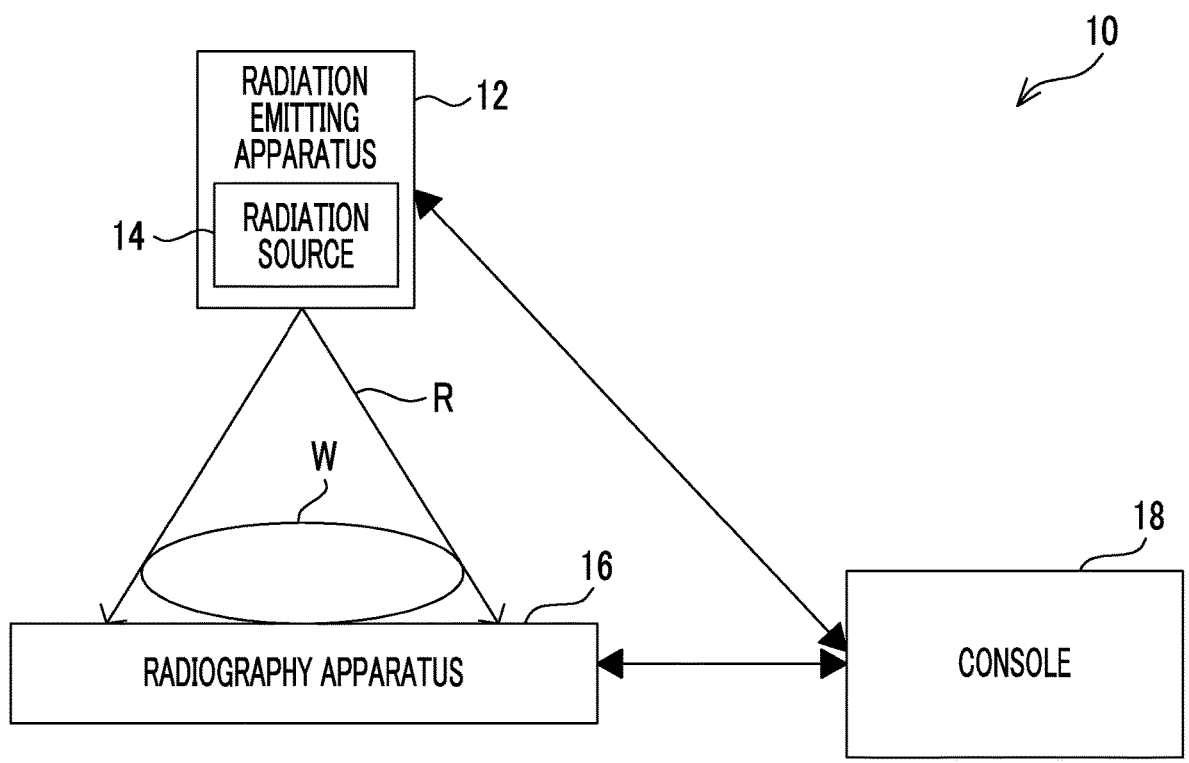
FIG. 1 is a block diagram illustrating an example of the configuration of a radiography system according to each embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a radiology technician, may press the irradiation button to command the emission of the radiation R such that the radiation R is emitted from the radiation emitting apparatus 12. In addition, for example, the user, such as a radiology technician, may operate the console 18 to command the emission of the radiation R such that the radiation R is emitted from the radiation emitting apparatus 12.

When receiving the command to emit the radiation R, the radiation emitting apparatus 12 emits the radiation R from the radiation source 14 according to set emission conditions, such as a tube voltage, a tube current, and an irradiation period. Hereinafter, the dose of the radiation R is simply referred to as "the amount of radiation".

Figure 2:
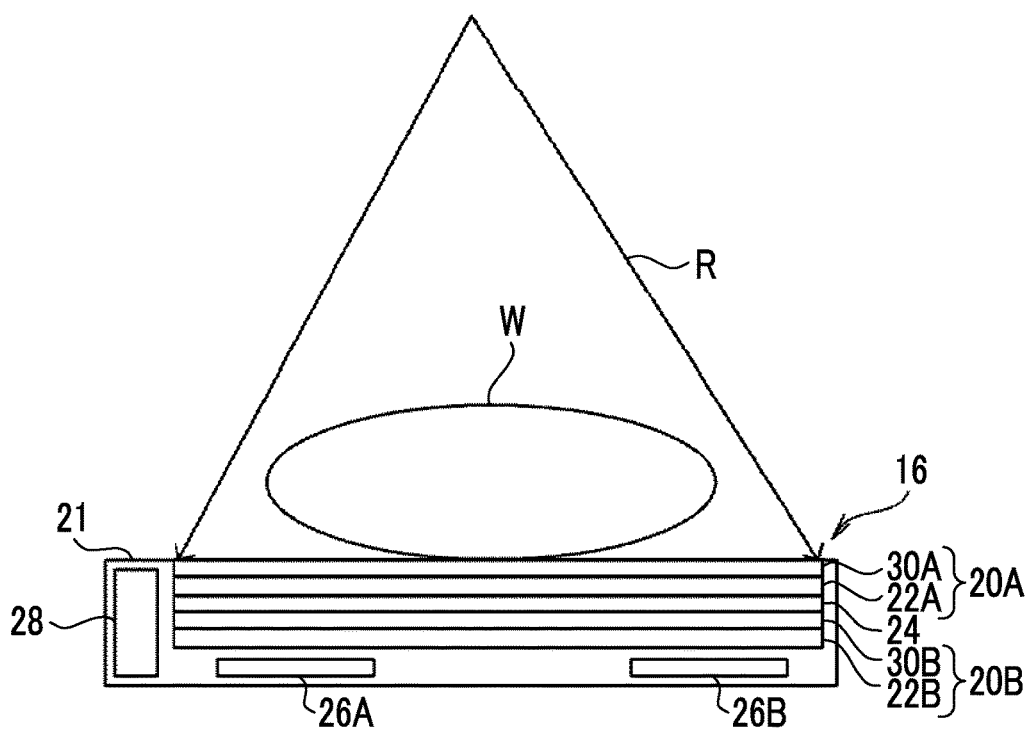
FIG. 2 is a side cross-sectional view illustrating an example of the configuration of a radiography apparatus according to a first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes a first radiation detector 20A and a second radiation detector 20B that detect the radiation R transmitted through the subject W. In addition, the housing 21 includes a radiation limitation member 24, a control substrate 26A, a control substrate 26B, and a case 28. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

The first radiation detector 20A is provided on the incident side of the radiation R and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) and the scintillator 22B includes gadolinium oxysulfide (GOS). In addition, a combination of the composition of the scintillator 22A and the composition of the scintillator 22B is not limited to the above-mentioned example and may be a combination of other compositions or a combination of the same compositions.

For example, the scintillators 22A and 22B have emission characteristics that vary depending on a thickness. As the thickness increases, the amount of light emitted increases and sensitivity increases. However, image quality is reduced due to, for example, light scattering.

For example, in a case in which the scintillators 22A and 22B are formed by being filled with particles which are irradiated with the radiation R and emit light, such as GOS particles, as the diameter of the particle increases, the amount of light emitted increases and sensitivity increases. However, the amount of light scattering increases and the increase in the amount of light scattering affects adjacent pixels 32 (see FIG. 3), which results in the deterioration of image quality.

In addition, the scintillators 22A and 22B may have a stacked structure of a small-particle layer and a large-particle layer. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the following phenomenon occurs. That is, in this case, in the scintillators 22A and 22B in which a region close to the irradiation side of the radiation R is filled with small particles and a region close to the side of the TFT substrate 30 that is the emission side of the radiation R is filled with large particles, image blurring is small. However, oblique components of light that is radially emitted by the small particles are less likely to reach the TFT substrates 30A and 30B and sensitivity is reduced. In addition, in a case in which the ratio of the region filled with small particles to the region filled with large particles is changed such that the number of layers formed by the region filled with large particles is larger than the number of layers formed by the region filled with small particles, sensitivity increases. However, in this case, light scattering affects adjacent pixels 32, which results in the deterioration of image quality.

As the filling rate of the particles increases, the sensitivity of the scintillators 22A and 22B increases. However, the amount of light scattering increases and image quality deteriorates. Here, the filling rate is a value obtained by dividing the total volume of the particles of the scintillator 22A or 22B by the volume of the scintillator 22A or 22B and multiplying the divided value by 100 (the total volume of the particles of the scintillator 22A or 22B/the volume of the scintillator 22A or 22B×100). In addition, powder is treated in the scintillators 22A and 22B. Therefore, in a case in which the filling rate is greater than 80%, it is difficult to manufacture the scintillators 22A and 22B. For this reason, it is preferable that the filling rate is in the range of 50 vol % to 80 vol %.

In addition, the emission characteristics of the scintillators 22A and 22B vary depending on the doping amount of activator. As the doping amount of activator increases, the amount of light emitted tends to increase. However, the amount of light scattering increases and image quality deteriorates.

The emission characteristics of the scintillators 22A and 22B with respect to the radiation R vary depending on the material used for the scintillators 22A and 22B. For example, in a case in which each of the first radiation detector 20A and the second radiation detector 20B is irradiated with the radiation R from the scintillators 22A and 22B to the TFT substrates 30A and 30B unlike the radiography apparatus 16 according to this embodiment, the scintillator 22A is made of GOS and the scintillator 22B is made of CsI (Tl) in order to put emphasis on sensitivity in the scintillator 22A and to put emphasis on image quality in the scintillator 22B.

In addition, the emission characteristics of the scintillators 22A and 22B with respect to the radiation R vary depending on whether the scintillators 22A and 22B have a plate-shaped layer structure or a columnar separated layer structure.

For example, the scintillator 22A is configured to have the plate-shape layer structure and the scintillator 22B is configured to have the columnar separated layer structure in order to put emphasis on sensitivity in the scintillator 22A and to put emphasis on image quality in the scintillator 22B.

In a case in which reflecting layers that transmit the radiation R and reflect visible light are formed on the sides of the TFT substrates 30A and 30B which are opposite to the scintillators 22A and 22B, light generated by the scintillators 22A and 22B is more effectively guided to the TFT substrates 30A and 30B and sensitivity is improved. A method for forming the reflecting layer is not particularly limited. For example, any of a sputtering method, a vapor deposition method, and a coating method may be used to form the reflecting layer. It is preferable that the reflecting layer is made of a material with high reflectance in an emission wavelength range of the scintillators 22A and 22B used. For example, the reflecting layer is made of Au, Ag, Cu, Al, Ni, and Ti. For example, in a case in which the scintillators 22A and 22B are made of GOS:Tb, the reflecting layer is preferably made of Ag, Al, and Cu that have high reflectance in a wavelength of 400 nm to 600 nm. In a case in which the thickness of the reflecting layer is less than 0.01 µm, reflectance is not obtained. Even in a case in which the thickness is greater than 3 µm, the effect of further improving the reflectance is not obtained. For this reason, it is preferable that the thickness of the reflecting layer is in the range of 0.01 µm to 3 µm.

Therefore, the characteristics of the scintillators 22A and 22B may vary depending on the diameter of particles, the multi-layered structure of particles, the filling rate of particles, the doping amount of activator, a material, a change in layer structure, and the shape of the reflecting layer.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that the thickness of the plate-shaped member is uniform in the range in which the error of a variation in the thickness is equal to or less than 1%. In a case in which the first radiation detector 20A sufficiently absorbs the radiation R, the radiation limitation member 24 may not be provided.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

The case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
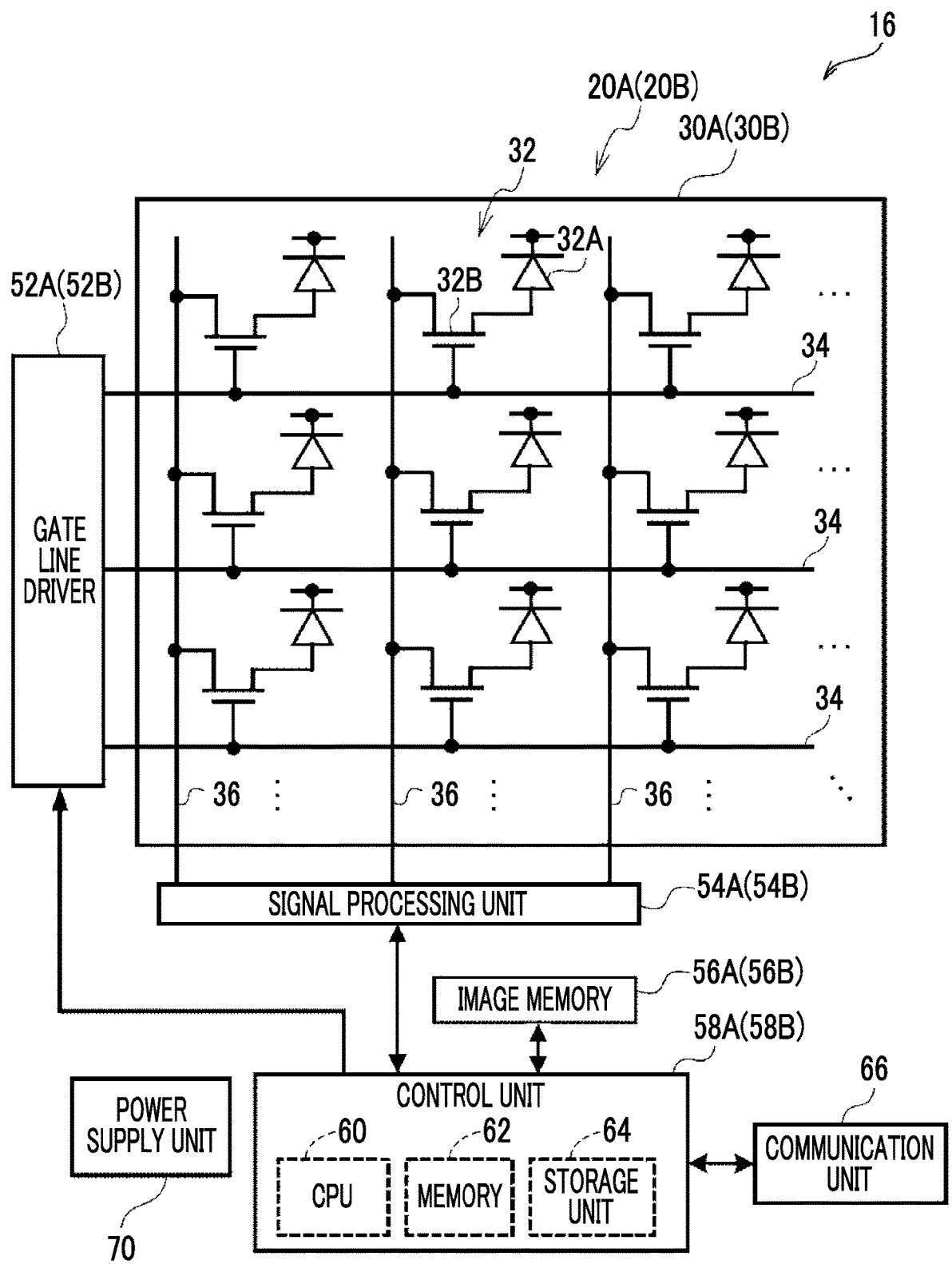
FIG. 3 is a block diagram illustrating an example of the configuration of a main portion of an electric system of a radiography apparatus according to each embodiment.

As illustrated in FIG. 3, a plurality of pixels 32 are two-dimensionally provided in one direction (a row direction in FIG. 3) and a cross direction (a column direction in FIG. 3) that intersects the one direction on the TFT substrate 30A. The pixel 32 includes a sensor unit 32A and a field effect thin film transistor (TFT; hereinafter, simply referred to as a "thin film transistor") 32B.

The sensor unit 32A includes, for example, an upper electrode, a lower electrode, and a photoelectric conversion film which are not illustrated, absorbs the light emitted from the scintillator 22A, generates charge, and accumulates the generated charge. The thin film transistor 32B converts the charge accumulated in the sensor unit 32A into an electric signal and outputs the electric signal. The sensor unit 32A is an example of a conversion element that generates a larger amount of charge as the amount of radiation becomes larger.

A plurality of gate lines 34 which extend in the one direction and are used to turn each thin film transistor 32B on and off are provided on the TFT substrate 30A. In addition, a plurality of data lines 36 which extend in the cross direction and are used to read out the charge through the thin film transistors 32B in an on state are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The rows of the thin film transistors 32B of the TFT substrate 30A are sequentially turned on by the electric signals which are supplied from the gate line driver 52A through the gate lines 34. Then, the charge which has been read by the thin film transistor 32B in an on state is transmitted as an electric signal through the data line 36 and is input to the signal processing unit 54A. In this way, charge is sequentially read from each row of the thin film transistors and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer and an analog/digital (A/D) converter are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

The control unit 58A which will be described below is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data".

Figure 4:
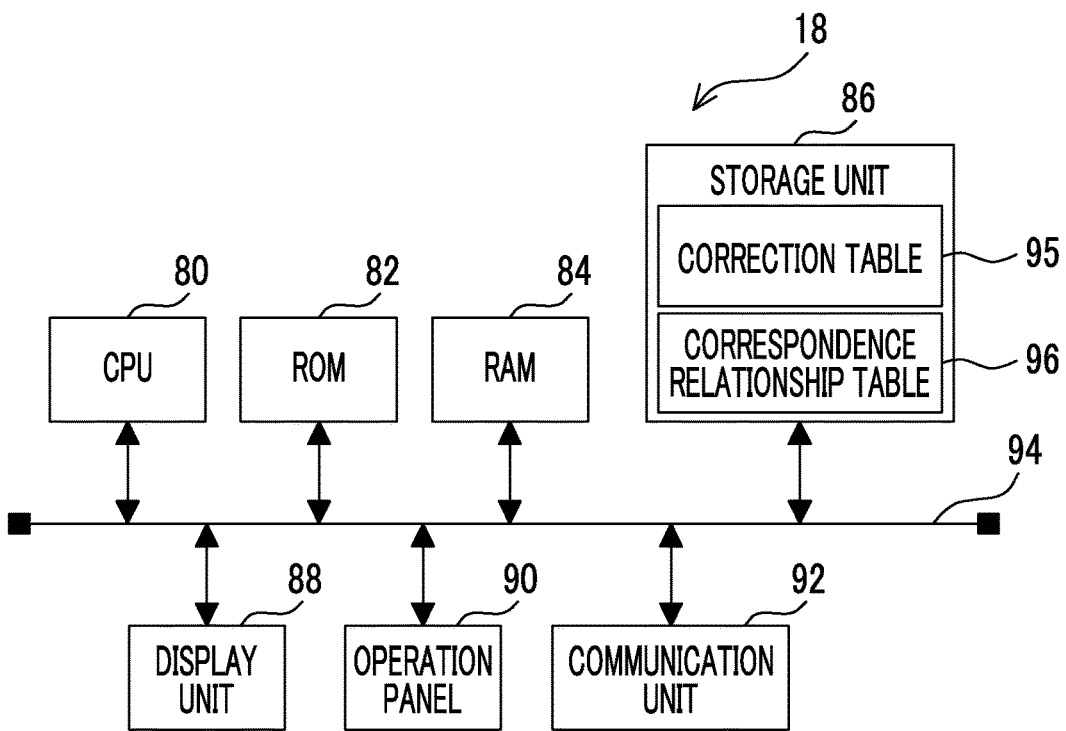
FIG. 4 is a block diagram illustrating an example of the configuration of a main portion of an electric system of a console according to each embodiment.

Next, the configuration of the console 18 according to this embodiment will be described with reference to FIG. 4. As illustrated in FIG. 4, the console 18 includes a CPU 80 that controls the overall operation of the console 18 and a ROM 82 in which, for example, various programs or various parameters are stored in advance. In addition, the console 18 includes a RAM 84 that is used as, for example, a work area when the CPU 80 executes various programs and a non-volatile storage unit 86 such as a hard disk drive (HDD).

The console 18 further includes a display unit 88 that displays, for example, an operation menu and a captured radiographic image and an operation panel 90 which includes a plurality of keys and to which various kinds of information or operation commands are input. In addition, the console 18 includes a communication unit 92 that transmits and receives various kinds of information to and from the external apparatuses, such as the radiation emitting apparatus 12 and the radiography apparatus 16, using at least one of wireless communication or wired communication. The CPU 80, the ROM 82, the RAM 84, the storage unit 86, the display unit 88, the operation panel 90, and the communication unit 92 are connected to each other through a bus 94.

A correction table 95 that is used for correction when the bone density of the subject W is derived and a correspondence relationship table 96 that is used to estimate the body thickness of the subject W are stored in the storage unit 86 in advance. The correction table 95 and the correspondence relationship table 96 will be described in detail below.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of soft-ray components than hard-ray components in energy forming the radiation R, which depends on the material forming the radiation limitation member 24. Therefore, the energy distribution of the radiation R that reaches the second radiation detector 20B has a larger number of hard-ray components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image. Since the absorptivity of radiation by the radiation detector 20 and the radiation limitation member 24 varies depending on the energy of the radiation R, the shape of a spectrum changes.

That is, the amount of radiation used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
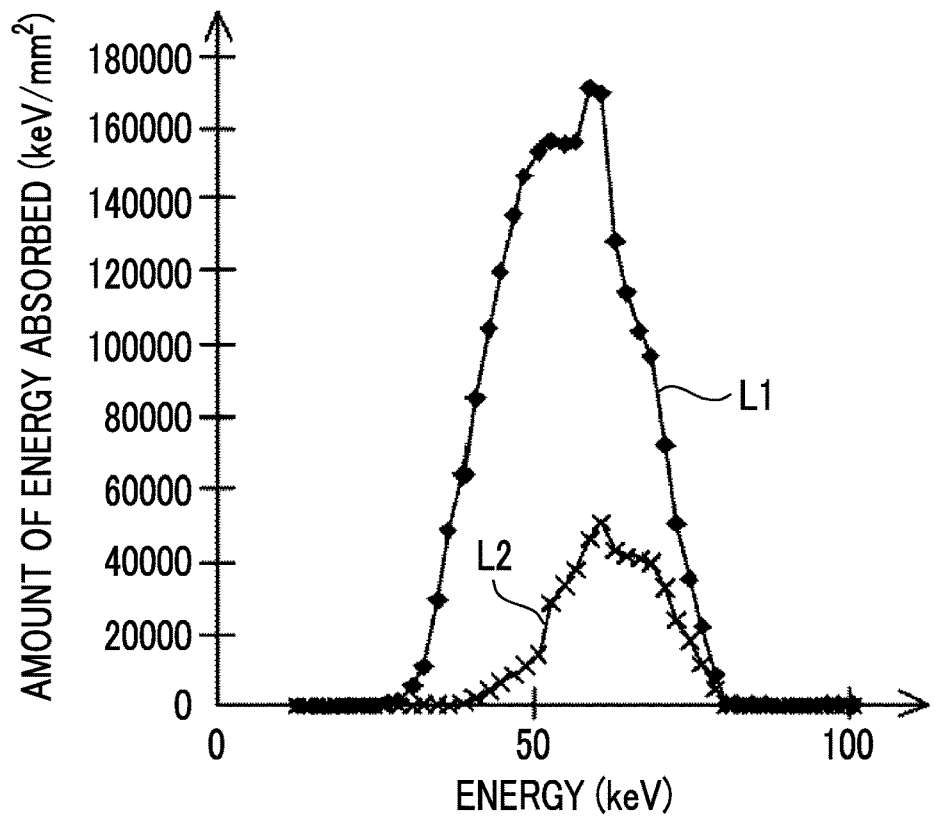
FIG. 5 is a graph illustrating the amount of radiation that reaches each of a first radiation detector and a second radiation detector.

Low-energy components of the radiation R are absorbed first. The radiation R absorbed by each of the first radiation detector 20A and the second radiation detector 20B will be described with reference to FIG. 5. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In addition, in FIG. 5, a solid line L2 indicates the relationship between the energy of the radiation R absorbed by the second radiation detector 20B and the amount of radiation R absorbed per unit area. Since the low-energy components of the radiation R are absorbed first, for example, as illustrated in FIG. 5, the energy components of the radiation R that reaches the second radiation detector 20B do not include the low-energy components of the energy components of the radiation R that reaches the first radiation detector 20A. That is, the energy of the radiation R emitted to the first radiation detector 20A is different from the energy of the radiation R emitted to the second radiation detector 20B through the first radiation detector 20A. Therefore, in the radiography apparatus 16 according to this embodiment, the radiation detectors 20 are irradiated with the radiations R having different energy levels and radiographic images are generated by the radiation detectors 20.

The console 18 according to this embodiment acquires radiographic image data generated by the radiation detectors 20 irradiated with the radiations R having different energy levels. In addition, the console 18 derives the ratio of the values of the corresponding pixels of first radiographic image data and second radiographic image data and generates image data for deriving the bone density of the subject W. Hereinafter, the image data for deriving the bone density of the subject W is referred to as "dual-energy X-ray absorptiometry (DXA) image data" and an image indicated by the DXA image data is referred to as a "DXA image". Specifically, the console 18 performs log conversion for each pixel value of each of the first radiographic image data and the second radiographic image data. Then, the console 18 subtracts image data obtained by performing log conversion for the second radiographic image data from image data obtained by performing log conversion for the first radiographic image data for each corresponding pixel to generate DXA image data.

Figure 6:
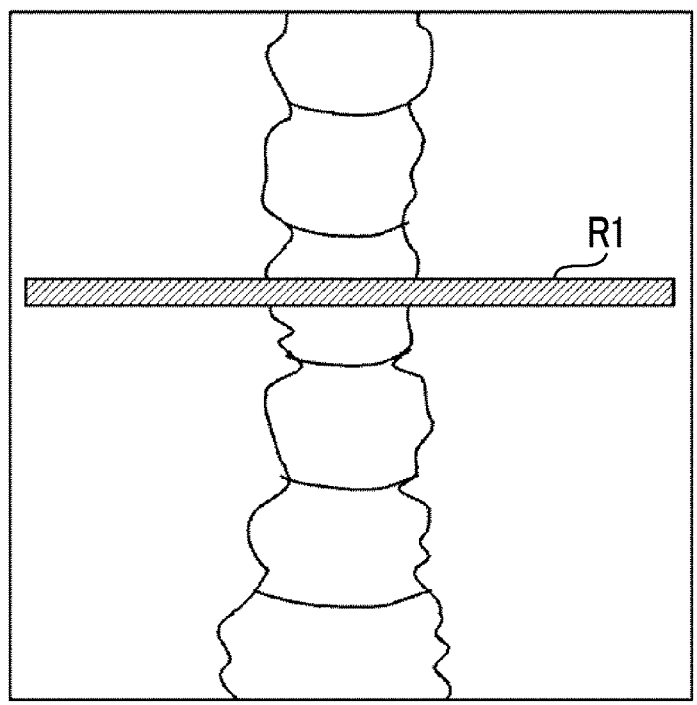
FIG. 6 is a front view illustrating an example of a region from which a DXA profile used to derive bone density is to be derived.

In addition, for example, as illustrated in FIG. 6, the console 18 according to this embodiment derives bone density from each pixel value (that is, the ratio of the values of the corresponding pixels of the first radiographic image and the second radiographic image) of the bone of the subject W in the DXA image in the cross-sectional direction (the horizontal direction in the example illustrated in FIG. 6).

Figure 7:
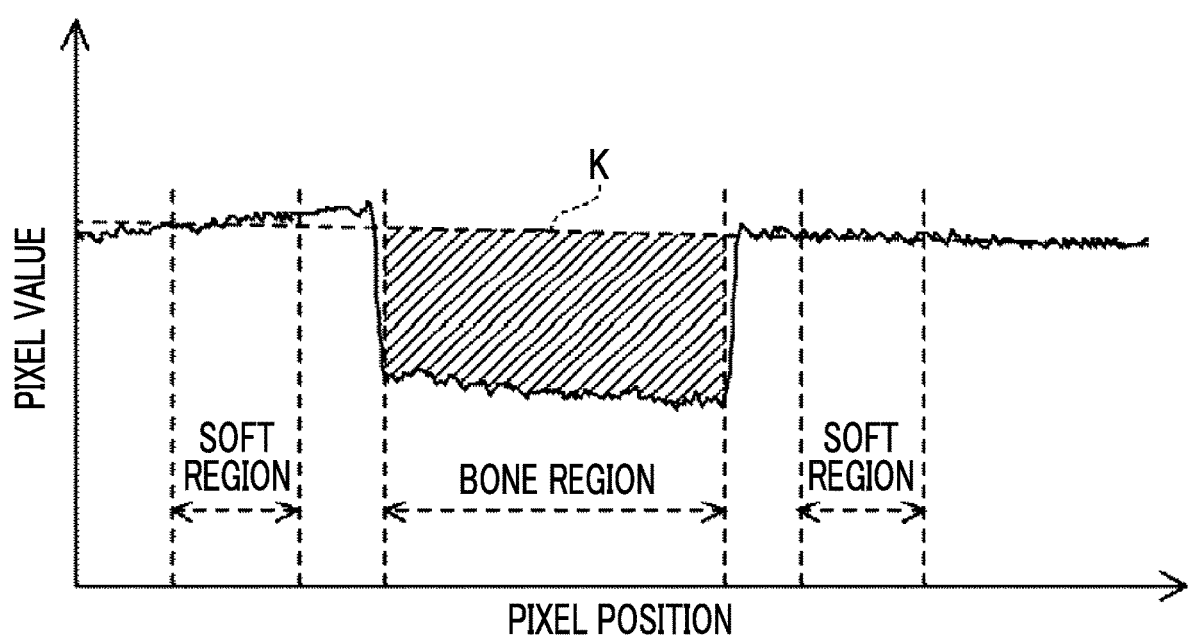
FIG. 7 is a graph illustrating a bone density derivation process.

FIG. 7 illustrates the value of each pixel in a region R1 of the DXA image illustrated in FIG. 6. In FIG. 7, the horizontal axis indicates a pixel position in the horizontal direction of FIG. 6. In addition, in FIG. 7, the vertical axis indicates the average value of the values of a plurality of pixels in the vertical direction of FIG. 6 at each pixel position in the horizontal direction of FIG. 6. Hereinafter, a data group of the pixel values at each pixel position along the horizontal direction of FIG. 6 which is illustrated in FIG. 7 is referred to as a "DXA profile".

As illustrated in FIG. 7, for the pixel values in the DXA profile, a pixel value at a pixel position corresponding to the bone tissue of the subject W is less than a pixel value at a pixel position corresponding to the soft tissue. The console 18 according to this embodiment derives the average value of the pixel values in each of soft tissue regions (hereinafter, referred to as "soft regions") on both sides of a bone tissue region (hereinafter, referred to as a "bone region") and derives a straight line (hereinafter, referred to as a "reference line") K that connects the average values derived at the pixel positions in a central portion of each soft region. In addition, the console 18 adds the differences between the reference line K and the pixel values at each pixel position in the bone region to derive the area of the bone region (the area of a hatched portion illustrated in FIG. 7). The area is a value corresponding to the bone mass of the subject W. For example, the bone region is separated from the soft region by a predetermined number of pixels in FIG. 7 in order to prevent the influence of noise caused by light scattered by the bone.

In addition, the console 18 divides the derived area by the number of pixels corresponding to the width of the bone region to derive the difference between the pixel values of the bone region and the soft region per unit number of pixels. The difference is a value corresponding to the bone density of the subject W. Then, the console 18 multiplies the derived difference between the pixel values of the bone region and the soft region per unit number of pixels by a predetermined unit conversion coefficient to derive the bone density of the subject W. In this embodiment, the pixel position of the region R1 used to derive the DXA profile in the DXA image data, the pixel position of the soft region in the DXA profile, and the pixel position of the bone region are predetermined according to, for example, the subject W and an imaging part.

Figure 8:
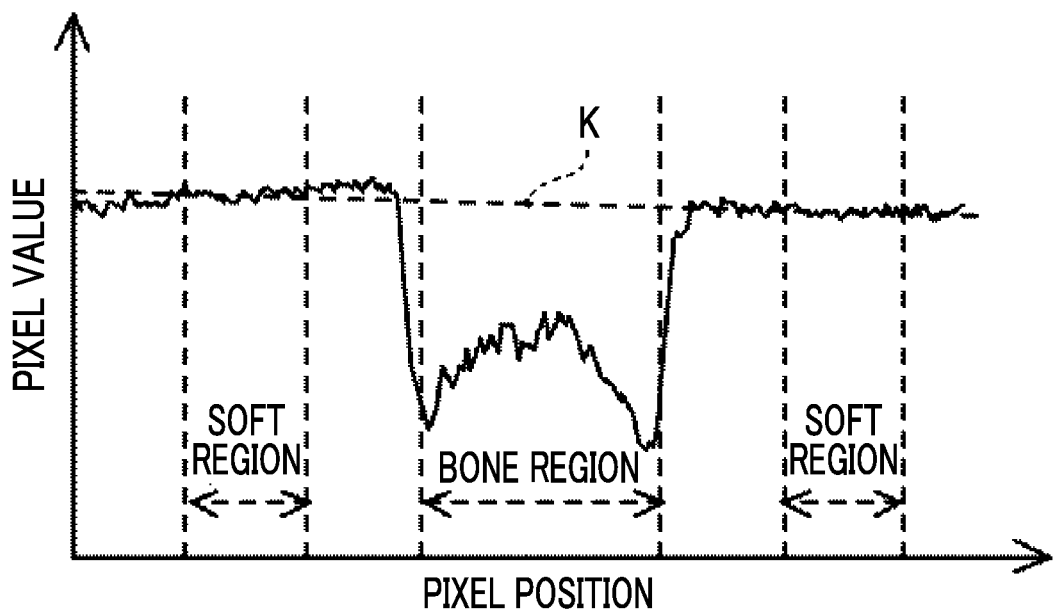
FIG. 8 is a graph illustrating an example of a DXA profile at a first body thickness.
Figure 9:
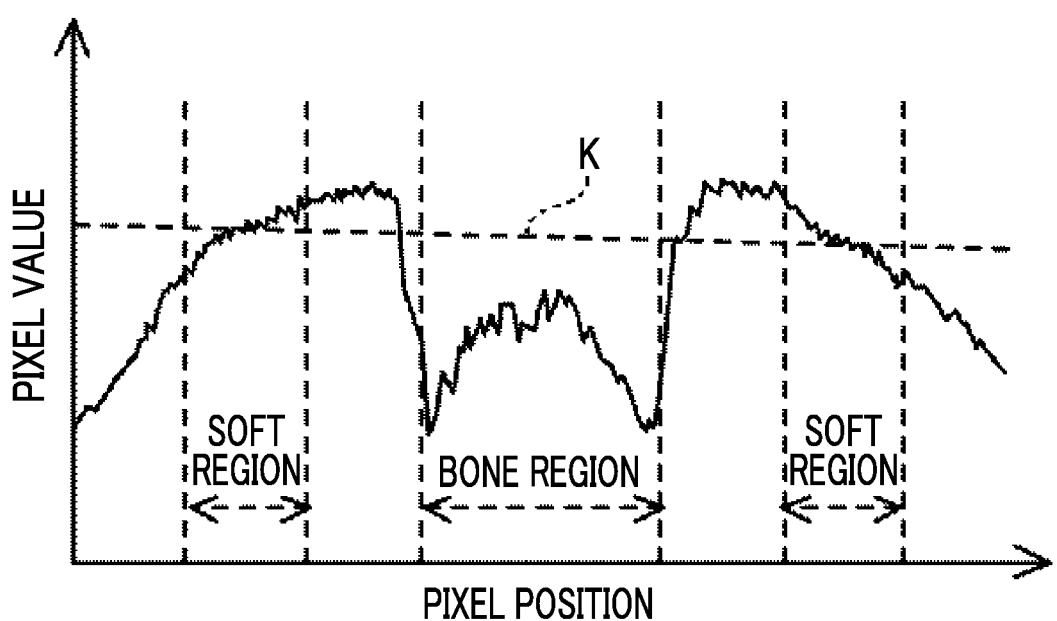
FIG. 9 is a graph illustrating an example of a DXA profile at a second body thickness.

Next, the DXA profile of a plurality of different body thicknesses will be described with reference to FIGS. 8 and 9. FIGS. 8 and 9 illustrate an example of the DXA profile obtained by capturing a radiographic image of a phantom that simulates a person, using a material corresponding to the soft tissue of the person and a material corresponding to the bone tissue. For example, acryl and urethane can be applied as the material corresponding to the soft tissue of the person. For example, hydroxyapatite can be applied as the material corresponding to the bone tissue of the person.

FIGS. 8 and 9 illustrate an example of the DXA profile in a case in which the thickness of the material corresponding to only the soft tissue of the bone tissue and the soft tissue is changed to change the body thickness. FIG. 8 illustrates an example of the DXA profile in a case in which the body thickness is a first body thickness (for example, 15 cm) and FIG. 9 illustrates an example of the DXA profile in a case in which the body thickness is a second body thickness (for example, 30 cm) greater than the first body thickness.

Since the same material is used for the bone tissues, it is preferable that the bone density derived using the DXA profile illustrated in FIG. 8 is equal to the bone density derived using the DXA profile illustrated in FIG. 9. However, as illustrated in FIGS. 8 and 9, the shape of the DXA profile varies depending on the body thickness. In particular, as the thickness of the soft tissue becomes larger, the quality of radiation becomes lower due to the oblique incidence of the radiation R in a region that is separated from the bone region of the radiographic image and the pixel value of the DXA image data becomes smaller. That is, in the soft region used to derive the bone density in the DXA profile, as the body thickness increases and as the distance from the bone region increases, the rate of decrease in the pixel value increases and the value of the intercept of the reference line K is reduced. Therefore, as the body thickness increases, the area of the bone region in the DXA profile is reduced. As a result, in some cases, it is difficult to accurately derive the bone density of the subject W.

For this reason, the console 18 according to this embodiment corrects the values of the pixels corresponding to the soft tissues in the DXA profile with correction data corresponding to the body thickness with reference to the correction table 95.

Figure 10:
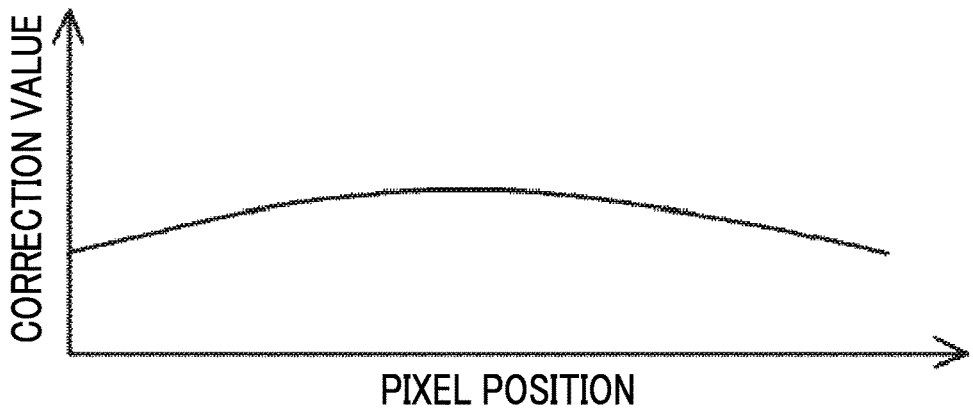
FIG. 10 is a graph illustrating an example of correction data according to each embodiment.

Next, the correction table 95 will be described with reference to FIGS. 10 to 12. Correction data corresponding to the body thickness is stored in the correction table 95 according to this embodiment. FIG. 10 illustrates an example of the correction data in a case in which the body thickness is 10 cm, FIG. 11 illustrates an example of the correction data in a case in which the body thickness is 20 cm, and FIG. 12 illustrates an example of the correction data in a case in which the body thickness is 30 cm.

Figure 11:
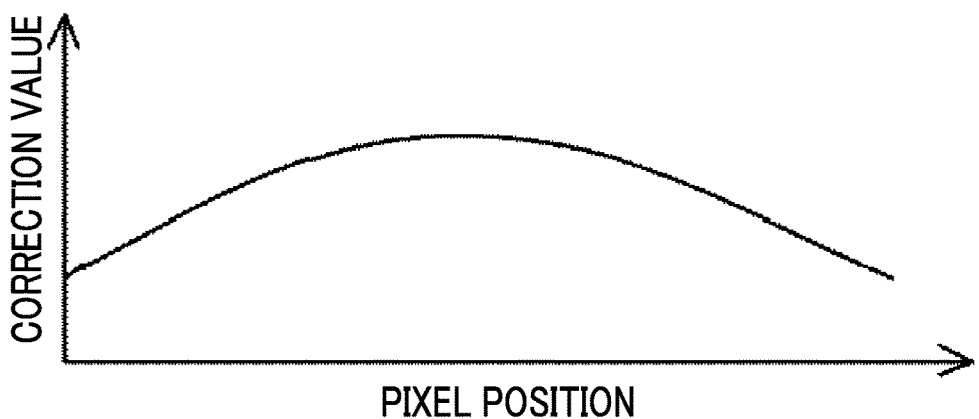
FIG. 11 is a graph illustrating an example of the correction data according to each embodiment.
Figure 12:
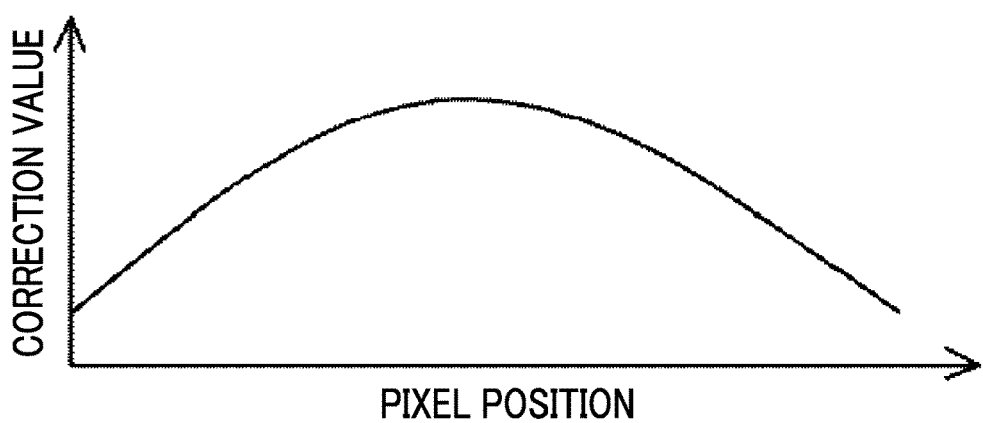
FIG. 12 is a graph illustrating an example of the correction data according to each embodiment.

As illustrated in FIGS. 10 to 12, the correction data according to this embodiment includes a correction value of each pixel corresponding to the DXA profile. In addition, for the correction values of the correction data, the correction value of the pixel corresponding to the soft tissue becomes smaller as the pixel position becomes further away from the pixel corresponding to the bone tissue. In addition, for the correction values of the correction data, as the body thickness increases, the difference between the correction value of the pixel corresponding to the soft tissue and the correction value of the pixel corresponding to the bone tissue increases. That is, the correction data according to this embodiment has an upward convex shape and has a larger gradient as the body thickness becomes larger. For example, radiographic images are captured while the thickness of the material corresponding to the soft tissue of the phantom is changed to change the body thickness of the phantom and DXA image data is generated for each body thickness from radiographic image data generated by each radiation detector 20. Then, correction data is derived for each body thickness on the basis of a DXA profile obtained from the generated DXA image data. The derived correction data is stored in the correction table 95 so as to be associated with the body thickness. The correction data is subtracted from the DXA profile for each corresponding pixel to correct the DXA profile, which will be described in detail below.

In addition, for example, the console 18 may acquire the correction table 95 from an external system connected through the network. Furthermore, only the correction value of the pixel position corresponding to the soft region used to derive the reference line K may be stored in the correction table 95.

The amount of radiation absorbed by the soft tissues of the subject W increases as the body thickness increases. That is, the pixel value of the soft region in the DXA image data decreases as the body thickness increase. For this reason, the console 18 according to this embodiment estimates the body thickness of the subject W from the value of the pixel corresponding to the soft tissue in the DXA image data with reference to the correspondence relationship table 96.

Figures 13, 14:
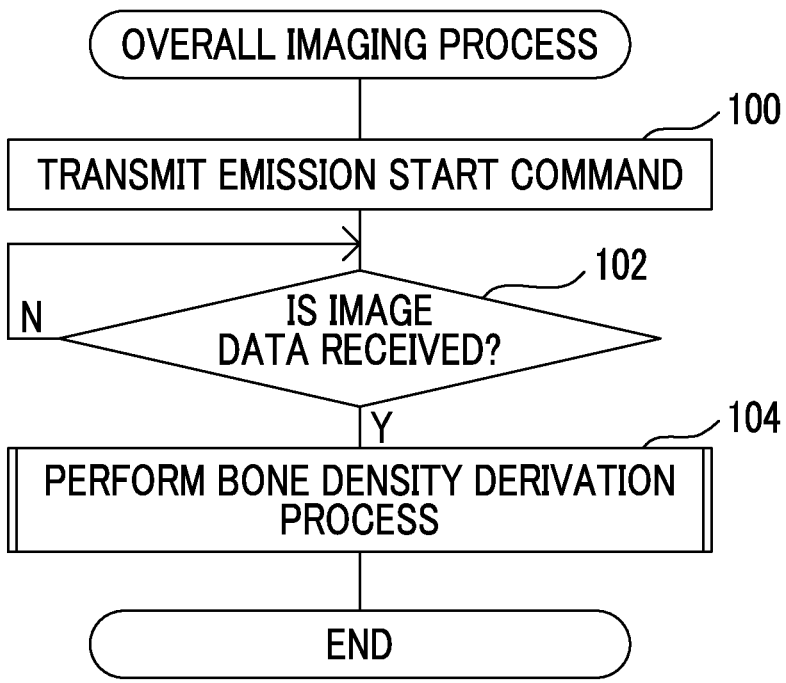
FIG. 13 is a graph illustrating an example of a correspondence relationship table according to each embodiment.
FIG. 14 is a flowchart illustrating the process flow of an overall imaging processing program according to the first embodiment.

Next, the correspondence relationship table 96 according to this embodiment will be described with reference to FIG. 13. As illustrated in FIG. 13, the value of the pixel corresponding to the soft tissue in the DXA image data is stored in the correspondence relationship table 96 so as to be associated with the body thickness. For example, the pixel value is derived and stored by the following process. That is, in this case, radiographic images are captured while the thickness of the material corresponding to the soft tissue of the phantom is changed to change the body thickness of the phantom and DXA image data is generated for each body thickness from radiographic image data generated by each radiation detector 20. Then, the average value of the pixel values of the soft region in the region R1 of the generated DXA image data is derived for each body thickness and the derived average value is stored in the correspondence relationship table 96 so as to be associated with the body thickness.

For example, FIG. 13 illustrates the correspondence relationship table 96 corresponding to the pixel position of the region R1 in the vertical direction in the DXA image illustrated in FIG. 6. In this embodiment, the correspondence relationship table 96 generated by shifting the region R1 in the vertical direction of the DXA image illustrated in FIG. 6 by a predetermined number of pixels is stored in the storage unit 86 so as to be associated with the pixel position in the vertical direction. That is, the console 18 according to this embodiment estimates the body thickness of the subject W from the value of the pixel corresponding to the soft tissue with reference to the correspondence relationship table 96 corresponding to the pixel position of the region R1 used to derive the DXA profile in the vertical direction in the DXA image.

In addition, for example, the console 18 may acquire the correspondence relationship table 96 from an external system connected to through the network.

Next, the operation of the radiography system 10 according to this embodiment will be described with reference to FIGS. 14 to 16. FIG. 14 is a flowchart illustrating the process flow of an overall imaging processing program executed by the CPU 80 of the console 18 in a case in which the user inputs the name of the subject W, an imaging part, and an imaging menu through the operation panel 90. The overall imaging processing program is installed in the ROM 82 of the console 18 in advance.

Figure 15:
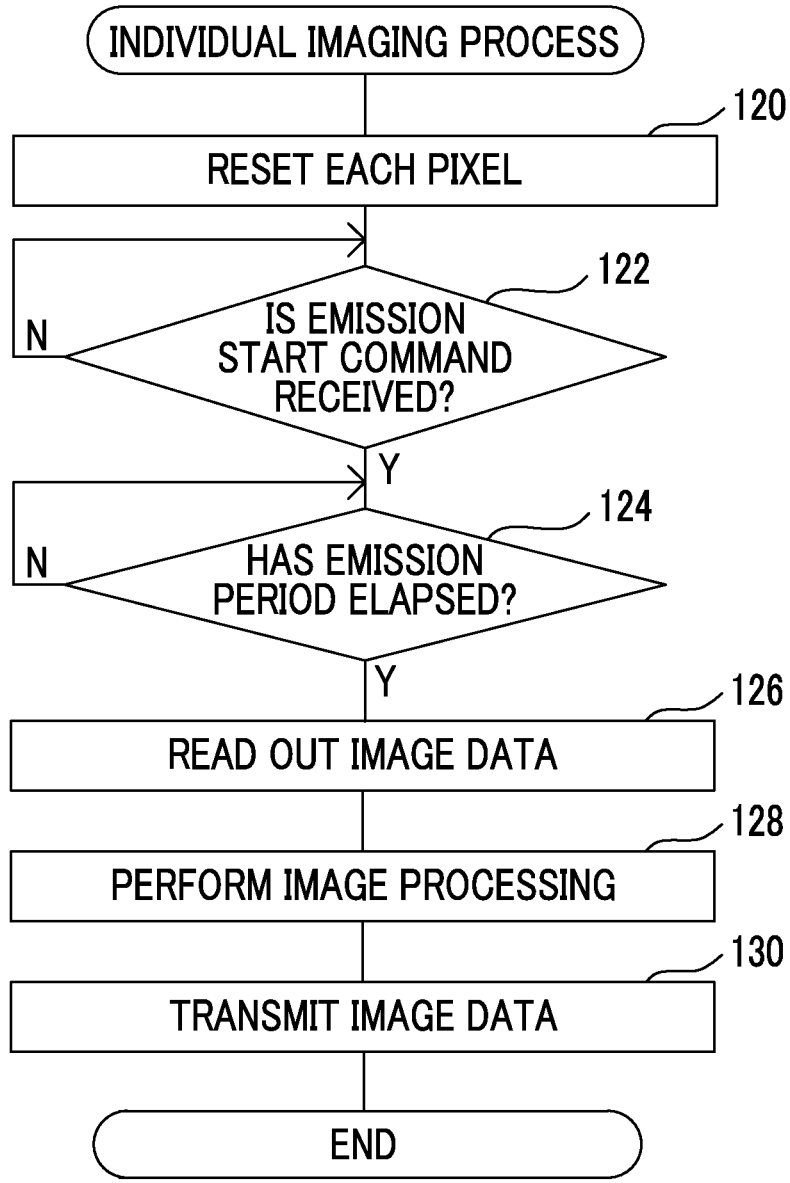
FIG. 15 is a flowchart illustrating the process flow of an individual imaging processing program according to the first embodiment.

FIG. 15 is a flowchart illustrating the process flow of an individual imaging processing program executed by the control unit 58A of the radiography apparatus 16 in a case in which the radiography apparatus 16 is turned on. The individual imaging processing program is installed in the ROM of the memory 62 of the control unit 58A in advance. In addition, the individual imaging processing program is installed in the ROM of the memory 62 of the control unit 58B in advance and is executed by the control unit 58B of the radiography apparatus 16 in a case in which the radiography apparatus 16 is turned on. In the individual imaging process illustrated in FIG. 15, the control unit 58A and the control unit 58B perform the same process. Therefore, hereinafter, only a case in which the individual imaging process is performed by the control unit 58A will be described and the description of a case in which the individual imaging process is performed by the control unit 58B will be omitted.

In Step 100 illustrated in FIG. 14, the CPU 80 transmits information included in the input imaging menu to the radiography apparatus 16 through the communication unit 92 and transmits the emission conditions of the radiation R to the radiation emitting apparatus 12 through the communication unit 92. Then, the CPU 80 transmits a command to start the emission of the radiation R to the radiography apparatus 16 and the radiation emitting apparatus 12 through the communication unit 92. When receiving the emission conditions and the emission start command transmitted from the console 18, the radiation emitting apparatus 12 starts the emission of the radiation R according to the received emission conditions. The radiation emitting apparatus 12 may include an irradiation button. In this case, the radiation emitting apparatus 12 receives the emission conditions and the emission start command transmitted from the console 18 and starts the emission of the radiation R according to the received emission conditions in a case in which the irradiation button is pressed.

Then, in Step 102, the CPU 80 waits until the first radiographic image data captured by the first radiation detector 20A and the second radiographic image data captured by the second radiation detector 20B are received. In a case in which the CPU 80 receives the first radiographic image data and the second radiographic image data through the communication unit 92, the determination result in Step 102 is "Yes" and the process proceeds to Step 104.

Figure 16:
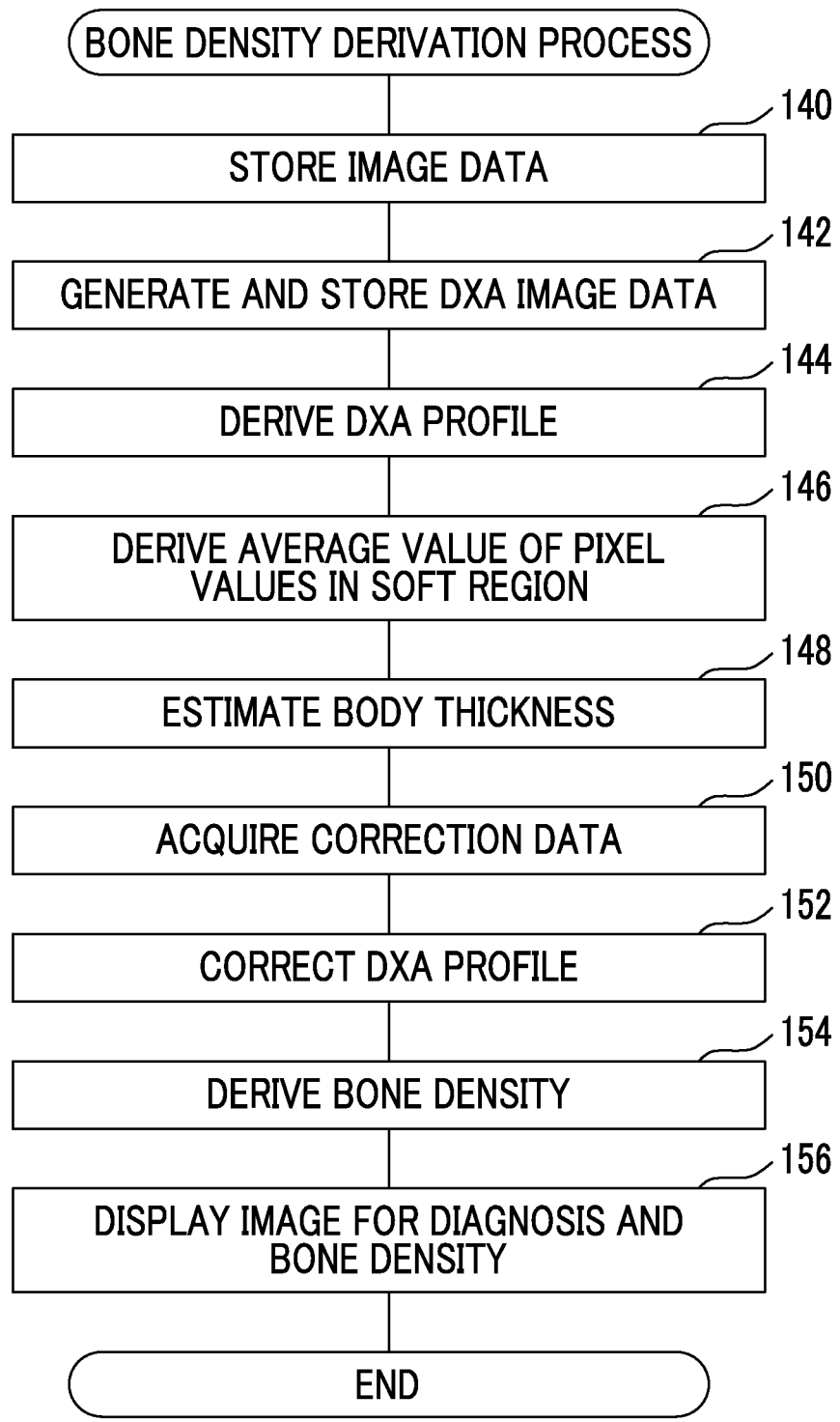
FIG. 16 is a flowchart illustrating the process flow of a bone density derivation processing program according to each embodiment.

In Step 104, the CPU 80 performs a bone density derivation process illustrated in FIG. 16 and ends the overall imaging process.

In Step 120 of FIG. 15, the control unit 58A performs a reset operation which extracts the charge accumulated in the sensor unit 32A of each pixel 32 in the first radiation detector 20A and removes the charge. In addition, the control unit 58A may perform the reset operation in Step 120 only once, may repeatedly perform the reset operation a predetermined number of times, or may repeatedly perform the reset operation until the determination result in Step 122, which will be described below, becomes "Yes".

Then, in Step 122, the control unit 58A waits until a command to start the emission of the radiation R is received. In a case in which the control unit 58A receives the emission start command transmitted from the console 18 in Step 100 of the overall imaging process through the communication unit 66, the determination result in Step 122 is "Yes" and the process proceeds to Step 124. In a case in which the radiation emitting apparatus 12 includes an irradiation button and the control unit 58A receives the emission start command transmitted from the console 18 and information indicating that the irradiation button has been pressed through the communication unit 66, the determination result in Step 122 is "Yes". For example, in a case in which the irradiation button is pressed, the radiation emitting apparatus 12 may directly transmit information indicating that the irradiation button has been pressed to the radiography apparatus 16 or may transmit the information to the radiography apparatus 16 through the console 18.

In Step 124, the control unit 58A waits for an emission period that is included in the information transmitted from the console 18 in Step 100 of the overall imaging process.

In Step 126, the control unit 58A controls the gate line driver 52A such that the gate line driver 52A sequentially outputs an on signal to each gate line 34 of the first radiation detector 20A for a predetermined period. Then, the rows of the thin film transistors 32B connected to each gate line 34 are sequentially turned on and the charge accumulated in each sensor unit 32A in each row sequentially flows as an electric signal to each data line 36. Then, the electric signal which has flowed to each data line 36 is converted into digital image data by the signal processing unit 54A and is stored in the image memory 56A.

Then, in Step 128, the control unit 58A performs image processing for performing various correction processes, such as offset correction and gain correction, for the image data stored in the image memory 56A in Step 126. Then, in Step 130, the control unit 58A transmits the image data (first radiographic image data) subjected to the image processing in Step 128 to the console 18 through the communication unit 66 and ends the individual imaging process.

In a case in which the console 18 receives the first radiographic image data and the second radiographic image data transmitted in Step 130, the determination result in Step 102 is "Yes" and the bone density derivation process illustrated in FIG. 16 is performed.

In Step 140 of FIG. 16, the CPU 80 stores the first radiographic image data and the second radiographic image data received in Step 102 in the storage unit 86. Then, in Step 142, the CPU 80 generates DXA image data using the first radiographic image data and the second radiographic image data received in Step 102.

As described above, the CPU 80 performs log conversion for each pixel value of each of the first radiographic image data and the second radiographic image data. Then, the CPU 80 subtracts image data obtained by the log conversion for the second radiographic image data from image data obtained by the log conversion for the first radiographic image data for each corresponding pixel to generate DXA image data. Then, the CPU 80 stores the generated DXA image data in the storage unit 86.

A method for determining the corresponding pixels of the first radiographic image data and the second radiographic image data is not particularly limited. For example, the amount of positional deviation between the first radiographic image data and the second radiographic image data, which are captured by the radiography apparatus 16 in a state in which a marker is put in advance, is calculated from the difference between the positions of the marker in the first radiographic image data and the second radiographic image data. Then, the corresponding pixels of the first radiographic image data and the second radiographic image data are determined on the basis of the calculated amount of positional deviation.

In this case, for example, the amount of positional deviation between the first radiographic image data and the second radiographic image data, which are obtained by capturing the image of both the subject W and the marker when the image of the subject W is captured, may be calculated from the difference between the positions of the marker in the first radiographic image data and the second radiographic image data. In addition, for example, the amount of positional deviation between the first radiographic image data and the second radiographic image data may be calculated on the basis of the structure of the subject W in the first radiographic image data and the second radiographic image data obtained by capturing the image of the subject W.

Then, in Step 144, the CPU 80 derives a DXA profile using the DXA image data generated in Step 142 as described above. Then, in Step 146, the CPU 80 derives the average value of pixel values in a soft region of the DXA profile generated in Step 144.

Then, in Step 148, the CPU 80 estimates the body thickness of the subject W on the basis of the average value of the pixel values derived in Step 146, with reference to the correspondence relationship table 96 corresponding to the pixel position of the region R1 used to derive the DXA profile in Step 144 in the vertical direction in the DXA image. For example, the CPU 80 estimates, as the body thickness of the subject W, a body thickness corresponding to a pixel value that is closest to the average value of the pixel values derived in Step 146 among the pixel values for each body thickness in the correspondence relationship table 96.

In addition, the CPU 80 may estimate the body thickness of the subject W from a pixel value that is closest to the average value of the pixel values derived in Step 146 and is greater than the average value and a pixel value that is closest to the average value and is less than the average value among the pixel values for each body thickness in the correspondence relationship table 96, using an interpolation process.

Then, in Step 150, the CPU 80 acquires correction data corresponding to the body thickness estimated in Step 148 with reference to the correction table 95. For example, the CPU 80 acquires correction data that is associated with a body thickness closest to the body thickness estimated in Step 148 among the correction data items for each body thickness in the correction table 95. In addition, the CPU 80 may derive correction data on the basis of correction data associated with a body thickness that is closest to the body thickness estimated in Step 148 and is greater than the estimated body thickness and correction data associated with a body thickness that is closest to the estimated body thickness and is less than the estimated body thickness among the correction data items for each body thickness, using the interpolation process.

Then, in Step 152, the CPU 80 corrects the DXA profile derived in Step 144 with the correction data acquired in Step 150. Specifically, the CPU 80 derives a pixel value NQL for normalization, according to the following Expression (1):

$$NQL = (RQL + LQL) \div 2.$$

In Expression (1), RQL indicates the average value of the pixel values in the soft region on one side (for example, the right side of FIG. 8) of the bone region in the DXA profile derived in Step 144. In Expression (1), LQL indicates the average value of the pixel values in the soft region on the other side (for example, the left side of FIG. 8) of the bone region in the DXA profile derived in Step 144.

The CPU 80 may derive, as the pixel value NQL for normalization, the average value of the pixel values in the soft region on the one side or the soft region on the other side. In addition, in a case in which the distance (that is, the number of pixels) from one end of the bone region to the soft region on the one side is different from the distance from the other end of the bone region to the soft region on the other side, the CPU 80 may derive the pixel value NQL for normalization as follows. That is, in this case, the CPU 80 may perform weighting according to the two different distances and then derive the pixel value NQL for normalization.

Figure 17:
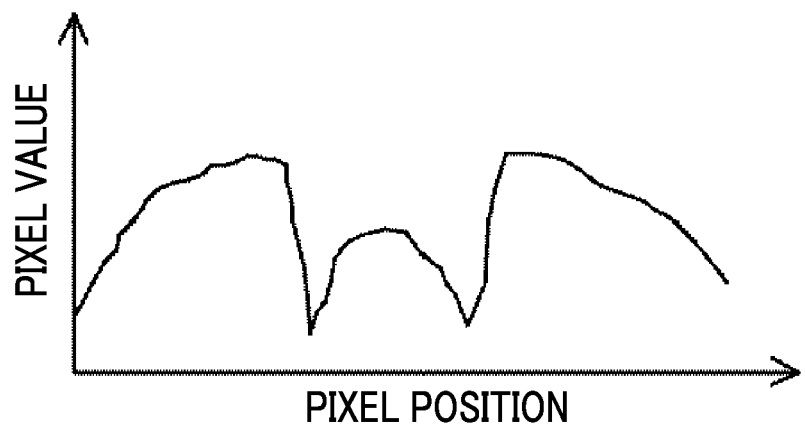
FIG. 17 is a graph illustrating an example of a DXA profile before correction.
Figure 18:
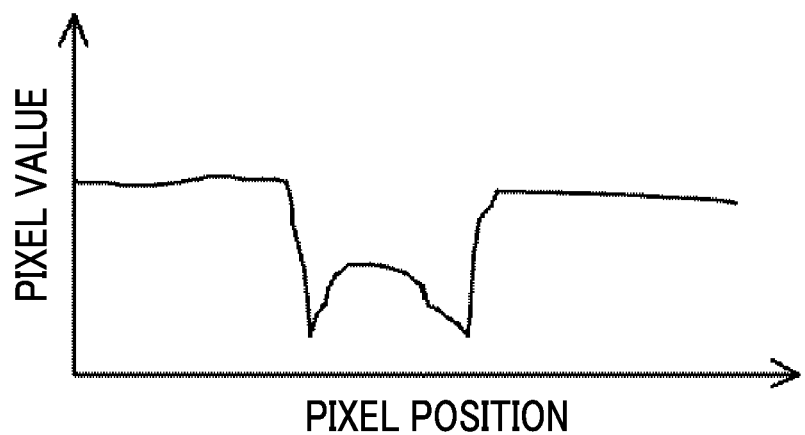
FIG. 18 is a graph illustrating an example of a corrected DXA profile.

Then, the CPU 80 subtracts the correction data acquired in Step 150 from the DXA profile derived in Step 144 for each corresponding pixel and adds the derived pixel value NQL for normalization to each pixel. For example, the shape of the DXA profile is corrected by the process in Step 152 as illustrated in FIGS. 17 and 18. FIG. 17 illustrates the DXA profile before correction derived in Step 144 and FIG. 18 illustrates the DXA profile corrected in Step 152. As illustrated in FIGS. 17 and 18, the shape of the soft region in the DXA profile is particularly corrected to a shape close to a horizontal shape, as compared to the shape before correction.

Then, in Step 154, the CPU 80 derives an integrated value of the differences between the reference line K and the pixel values of the bone region in the DXA profile corrected in Step 152. In addition, the CPU 80 divides the derived integrated value by the number of pixels corresponding to the width of the bone region in the corrected DXA profile. Then, the CPU 80 multiplies the value obtained by the division by the unit conversion coefficient to derive the bone density of the subject W.

In Step 156, the CPU 80 displays a first radiographic image indicated by the first radiographic image data received in Step 100 as an image for diagnosis on the display unit 88, displays the bone density derived in Step 154 on the display unit 88, and ends the bone density derivation process.

In addition, the CPU 80 may generate image data indicating an energy subtraction image (hereinafter, referred to as an "ES image"), using the first radiographic image data and the second radiographic image data received in Step 100. Hereinafter, the image data is referred to as "ES image data". In this case, for example, the CPU 80 subtracts image data obtained by multiplying the first radiographic image data by a predetermined coefficient from image data obtained by multiplying the second radiographic image data by a predetermined coefficient for each corresponding pixel. The CPU 80 generates ES image data indicating an ES image in which the soft tissues have been removed and the bone tissues have been highlighted, using the subtraction. In this example, in Step 156, the CPU 80 may display an ES image in which the bone tissues have been highlighted on the display unit 88, instead of the image for diagnosis.

In addition, the CPU 80 may specify the edge of a bone region in the ES image in which the bone tissues have been highlighted and may use the specification result as a pixel position corresponding to the bone region in the DXA image data. In this case, for example, the CPU 80 estimates the approximate range of the bone region on the basis of the imaging part included in the imaging menu. Then, the CPU 80 detects pixels that are disposed in the vicinity of the pixels, of which the differential values are equal to or greater than a predetermined value, as the pixels forming the edge (end) of the bone region in the estimated range to specify the bone region.

In this case, the CPU 80 may specify, as the soft region, a region which has a predetermined area including pixels that are separated from the specified edge of the bone region by a distance corresponding to a predetermined number of pixels in a predetermined direction in which the region becomes further away from the edge. In this case, the CPU 80 may use the specification result as a pixel position corresponding to the soft tissue in the DXA image data.

As described above, according to this embodiment, the ratio of the pixel values in a region, which corresponds to the soft tissue of the subject W and is a corresponding region of the radiographic images generated by the radiation detectors 20 irradiated with the radiations R having different energy levels is corrected using the correction data corresponding to the body thickness. Therefore, it is possible to accurately derive the bone density of the subject W, using each of the radiographic images generated by emitting radiations R having different energy levels. In addition, for example, the absorptivity of the radiation R in the soft tissues of the subject W is different in muscle and fat. In this embodiment, since the body thickness is estimated using the ratio of the pixel values in the region corresponding to the soft tissues of the subject W, it is possible to derive bone density, considering the physical constitution of the subject W.

In addition, according to this embodiment, the bone density of the subject W is derived using the radiographic images generated by two radiation detectors 20 of the radiography apparatus 16. Therefore, the bone density of the subject W can be derived by one operation of emitting the radiation R. As a result, it is possible to derive the bone density of the subject W while reducing the amount of radiation R emitted to the subject W.

Second Embodiment

Next, a second embodiment of the present disclosure will be described in detail below. Since a radiography system 10 according to this embodiment has the same configuration as the radiography system according to the first embodiment except the configuration of the radiography apparatus 16 (see FIGS. 1, 3, and 4), the description thereof will not be repeated in this embodiment. In addition, components having the same functions as those in the first embodiment are denoted by the same reference numerals and the description thereof will not be repeated.

Figure 19:
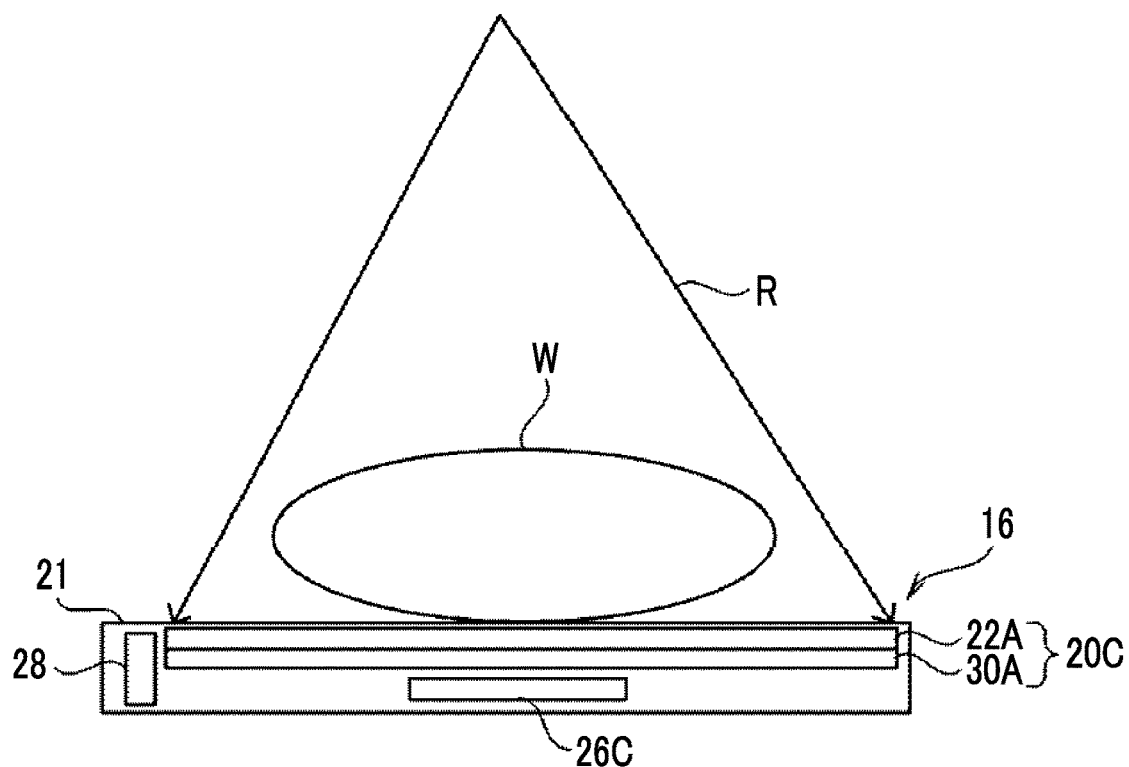
FIG. 19 is a side cross-sectional view illustrating an example of the configuration of a radiography apparatus according to a second embodiment.

As illustrated in FIG. 19, a radiation detector 20C that detects radiation R transmitted through a subject W and a control substrate 26C are provided in the housing 21 of the radiography apparatus 16 according to this embodiment. Since the configuration of the radiation detector 20C is the same as that of the first radiation detector 20A according to the first embodiment, the description thereof will not be repeated in this embodiment. In addition, since the configuration of the control substrate 26C is the same as that of the control substrate 26A according to the first embodiment, the description thereof will not be repeated in this embodiment.

Figure 20:
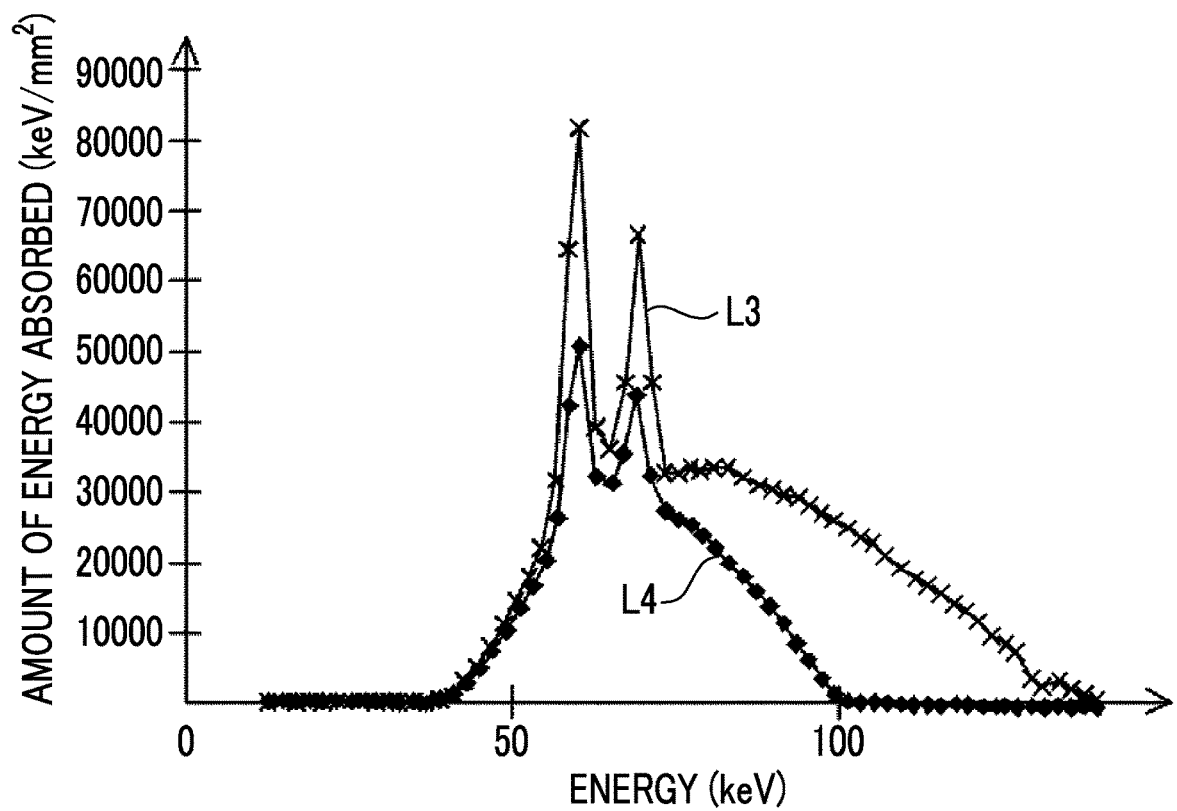
FIG. 20 is a graph illustrating the amount of radiation absorbed by a radiation detector in a case in which radiation is emitted at different tube voltages.

The radiography system 10 according to this embodiment performs two radiographic image capture operations with different tube voltages and derives bone density, using each radiographic image data item obtained from the radiation detector 20C by two imaging operations. Since the tube voltage is different in the two imaging operations, the radiation detector 20C is irradiated with the radiations R having different energy levels. The radiation R absorbed by the radiation detector 20C will be described with reference to FIG. 20. In FIG. 20, the vertical axis indicates the amount of radiation R absorbed per unit area and the horizontal axis indicates the energy of the radiation R. In addition, in FIG. 20, a solid line L3 indicates the relationship between the energy of the radiation R absorbed by the radiation detector 20C and the amount of radiation R absorbed per unit area in a case in which the tube voltage of the radiation source 14 is 140 kV. In FIG. 20, a solid line L4 indicates the relationship between the energy of the radiation R absorbed by the radiation detector 20C and the amount of radiation R absorbed per unit area in a case in which the tube voltage of the radiation source 14 is 100 kV. As illustrated in FIG. 20, since the tube voltage of the radiation source 14 is different, the radiation detector 20C is irradiated with the radiations R having different energy levels in first irradiation and second irradiation.

Figure 21:
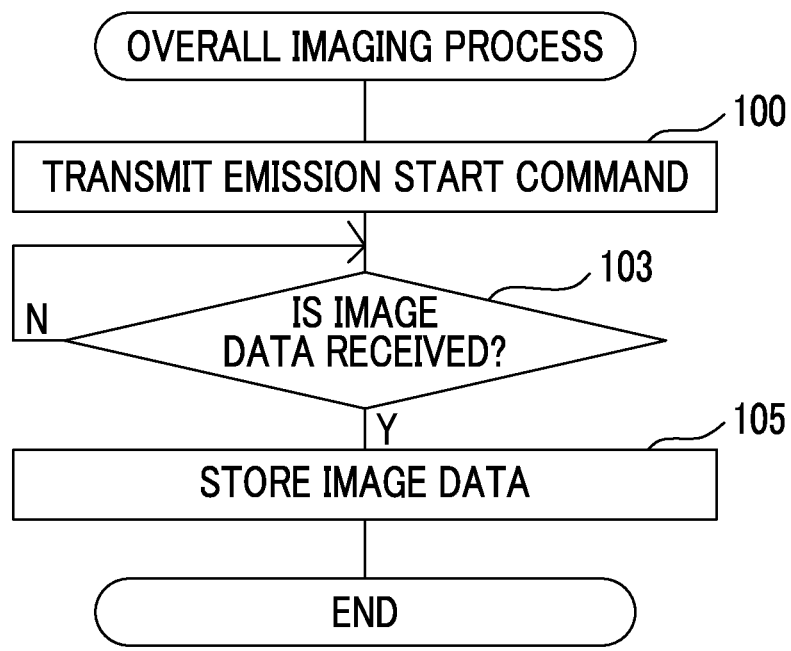
FIG. 21 is a flowchart illustrating the process flow of an overall imaging processing program according to the second embodiment.

Next, the operation of the radiography system 10 according to this embodiment will be described with reference to FIGS. 21 and 22. In FIG. 21, steps in which the same processes as those in FIG. 14 are performed are denoted by the same reference numerals as those in FIG. 14 and the description thereof will not be repeated. In FIG. 22, steps in which the same processes as those in FIG. 15 are performed are denoted by the same reference numerals as those in FIG. 15 and the description thereof will not be repeated.

In Step 103 of FIG. 21, the CPU 80 waits until radiographic image data captured by the radiation detector 20C is received. In a case in which the CPU 80 receives radiographic image data through the communication unit 92, the determination result in Step 103 is "Yes" and the process proceeds to Step 105. In Step 105, the CPU 80 stores the radiographic image data received in Step 103 in the storage unit 86 and ends the overall imaging process.

In this embodiment, the user operates the radiography system to perform the overall imaging process two times in a series of radiographic image capture processes. In this case, the user sets the tube voltage so as to be different in the first imaging operation and the second imaging operation. In this embodiment, a case in which the tube voltage (for example, 70 kV) in the first imaging operation is lower than the tube voltage in the second imaging operation and the tube voltage (for example, 100 kV) in the second imaging operation is higher than the tube voltage in the first imaging operation will be described. In addition, the tube voltage in the first imaging operation may be higher than the tube voltage in the second imaging operation.

In Step 131 of FIG. 22, the control unit 58A determines whether the process from Step 120 to Step 130 has been repeatedly performed two times. In a case in which the determination result is "No", the process returns to Step 120. In a case in which the determination result is "Yes", the individual imaging process ends.

The CPU 80 of the console 18 performs the following process, using the radiographic image data transmitted from the radiography apparatus 16 by the first process in Step 130 as the second radiographic image data. That is, in this case, the CPU 80 performs the same process as that from Step 142 to Step 156 in the bone density derivation process according to the first embodiment, using the radiographic image data transmitted from the radiography apparatus 16 by the second process in Step 130 as the first radiographic image data.

In this embodiment, the same radiography apparatus 16 as that according to the first embodiment may be used. In this case, for example, a DXA image is generated from each of the radiographic images generated by irradiating the first radiation detector 20A provided on the incident side of the radiation R with the radiations R having different energy levels.

As described above, according to this embodiment, it is possible to obtain the same effect as that in the first embodiment even in a radiography apparatus including one radiation detector.

In each of the above-described embodiments, the case in which log conversion is performed for each of the values of the corresponding pixels of the first radiographic image data and the second radiographic image data and the difference between the pixel values is calculated to derive the ratio of the values of the pixels has been described. However, the invention is not limited thereto. For example, each of the values of the corresponding pixels of the first radiographic image data and the second radiographic image data may be multiplied by a weighting coefficient, log conversion may be performed for each pixel value, and the difference between the pixel values may be calculated to derive the ratio of the values of the pixels. In this case, the weighting coefficient may be a value that is obtained in advance as a coefficient for accurately deriving bone density by, for example, experiments using the actual radiography apparatus 16. For example, in a case in which the imaging part includes a region (for example, a region corresponding to the intestinal canal) including gas, such as the abdomen, a weighting coefficient for removing the pixel value of the region including gas may be used.

In each of the above-described embodiments, the case in which the body thickness of the subject W is estimated from the pixel value of the pixel corresponding to the soft tissue in the DXA image data has been described. However, the invention is not limited thereto. For example, the body thickness of the subject W may be estimated from an image of the subject W captured by an imaging apparatus such as a camera. In addition, for example, the body thickness of the subject W may be measured by a length measuring device using ultrasonic waves. Furthermore, for example, the user may input the body thickness of the subject W through the operation panel 90.

In each of the above-described embodiments, the number of body thicknesses in the correspondence relationship table 96 is not limited to 5 and may be equal to or greater than 6 or equal to or less than 4.

In each of the above-described embodiments, the bone density derivation process performed by the console 18 may be performed by the control unit 58A or the control unit 58B of the radiography apparatus 16. In addition, in a case in which the radiography apparatus 16 includes an overall control unit that controls the overall operation of the control unit 58A and the control unit 58B, the overall control unit may perform the bone density derivation process. Furthermore, for example, an information processing apparatus that is connected to the console 18 through the network may perform the bone density derivation process.

In each of the above-described embodiments, the pixel value of the DXA image data and the body thickness which are associated with each other in a table format may be associated with each other by an arithmetic expression. Similarly, the correction data and the body thickness which are associated with each other in a table format may be associated with each other by an arithmetic expression.

In each of the above-described embodiments, the case in which the body thickness of the subject W is estimated on the basis of the average value of the pixel values in the soft region of the DXA profile has been described. However, the invention is not limited thereto. For example, the body thickness of the subject W may be estimated on the basis of representative values, such as the median and mode of the pixel values in the soft region of the DXA profile, other than the average value.

In the first embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B. In addition, for example, a conversion layer that absorbs radiation and converts the radiation into charge in the direct-conversion-type radiation detector is made of amorphous selenium (a-Se) and crystalline cadmium telluride (CdTe).

In the first embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In each of the above-described embodiments, the case in which bone density is derived using the first radiographic image data and the second radiographic image data has been described. However, the invention is not limited thereto. For example, bone mineral content or both bone density and bone mineral content may be derived using the first radiographic image data and the second radiographic image data.

In each of the above-described embodiments, the overall imaging process and the individual imaging process which are performed by the execution of software (program) by the CPU may be performed by various processors other than the CPU. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the overall imaging process and the individual imaging process may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the overall imaging processing program is stored (installed) in the ROM 82 in advance. However, the invention is not limited thereto. The overall imaging processing program may be recorded on a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through the network.

In each of the above-described embodiments, the aspect in which the individual imaging processing program is stored in the ROM of the memory 62 in the control unit 58A (control unit 58B) in advance has been described. However, the invention is not limited thereto. The individual imaging processing program may be recorded on the recording medium and then provided. In addition, the individual imaging processing program may be downloaded from an external apparatus through the network.

EXPLANATION OF REFERENCES

- 10: radiography system
- 12: radiation emitting apparatus
- 14: radiation source
- 16: radiography apparatus
- 18: console
- 20A: first radiation detector
- 20B: second radiation detector
- 20C: radiation detector
- 21: housing
- 22A, 22B: scintillator
- 24: radiation limitation member
- 26A, 26B, 26C: control substrate
- 28: case
- 30A, 30B: TFT substrate
- 32: pixel
- 32A: sensor unit
- 32B: thin film transistor
- 34: gate line
- 36: data line
- 52A, 52B: gate line driver
- 54A, 54B: signal processing unit
- 56A, 56B: image memory
- 58A, 58B: control unit
- 60, 80: CPU
- 62: memory
- 64, 86: storage unit
- 66, 92: communication unit
- 70: power supply unit
- 82: ROM
- 84: RAM
- 88: display unit
- 90: operation panel
- 94: bus
- 95: correction table
- 96: correspondence relationship table
- K: reference line
- L1, L2, L3, L4: solid line
- R: radiation
- R1: region
- W: subject

What is claimed is:

1. A radiography system comprising:
    a radiography apparatus including two radiation detectors in which a plurality of pixels, each of which includes a conversion element that generates a larger amount of charge as it is irradiated with a larger amount of radiation, are two-dimensionally arranged and which are arranged in a direction in which the radiation is emitted; and
    a controller including a processor and a memory coupled to the processor, wherein the processor is configured to:
    correct a ratio of pixel values in a region, which corresponds to a soft tissue of a subject and is a corresponding region of radiographic images generated by the two radiation detectors irradiated with radiations having different energy levels, on the basis of correction data corresponding to a body thickness, and
    derive at least one of bone density or bone mineral content of the subject on the basis of a difference between a ratio of pixel values in a region, which corresponds to a bone tissue of the subject and is a corresponding region of the radiographic images, and the ratio of the pixel values that has been corrected.

2. The radiography system according to claim 1,
    wherein the correction data includes a correction value for each pixel,
    the correction value of a region corresponding to the soft tissue becomes smaller as the pixel becomes further away from a region corresponding to the bone tissue, and
    a difference between the correction value of the region corresponding to the soft tissue and the correction value of the region corresponding to the bone tissue increases as the body thickness increases.

3. The radiography system according to claim 1, wherein the processor is configured to:
    estimate the body thickness of the subject on the basis of correspondence relationship information in which the body thickness is associated with the ratio of the pixel values in the region corresponding to the soft tissue.

4. The radiography system according to claim 1,
    wherein each of the two radiation detectors comprises a light emitting layer that is irradiated with radiation and emits light,
    the plurality of pixels of each of the two radiation detectors receive the light, generate the charge, and accumulate the charge, and
    the light emitting layer of one of the two radiation detectors which is provided on an incident side of the radiation includes CsI and the light emitting layer of the other radiation detector includes GOS.

5. A radiography system comprising:
    a radiography apparatus including a single radiation detector in which a plurality of pixels, each of which includes a conversion element that generates a larger amount of charge as it is irradiated with a larger amount of radiation, are two-dimensionally arranged; and
    a controller including a processor and a memory coupled to the processor, wherein the processor is configured to:
    correct a ratio of pixel values in a region, which corresponds to a soft tissue of a subject and is a corresponding region of radiographic images generated by the radiation detector irradiated with radiations having different energy levels, on the basis of correction data corresponding to a body thickness, and
    derive at least one of bone density or bone mineral content of the subject on the basis of a difference between a ratio of pixel values in a region, which corresponds to a bone tissue of the subject and is a corresponding region of the radiographic images, and the ratio of the pixel values that has been corrected.

6. A radiography method that is performed by a radiography apparatus including two radiation detectors in which a plurality of pixels, each of which includes a conversion element that generates a larger amount of charge as it is irradiated with a larger amount of radiation, are two-dimensionally arranged and which are arranged in a direction in which the radiation is emitted, the method comprising:

correcting a ratio of pixel values in a region, which corresponds to a soft tissue of a subject and is a corresponding region of radiographic images generated by the two radiation detectors irradiated with radiations having different energy levels, on the basis of correction data corresponding to a body thickness; and deriving at least one of bone density or bone mineral content of the subject on the basis of a difference between a ratio of pixel values in a region, which corresponds to a bone tissue of the subject and is a corresponding region of the radiographic images, and the corrected ratio of the pixel values.

7. A non-transitory computer readable medium storing a program that causes a computer to execute a process to control a radiography apparatus, the apparatus including two radiation detectors in which a plurality of pixels, each of which includes a conversion element that generates a larger amount of charge as it is irradiated with a larger amount of radiation, are two-dimensionally arranged and which are arranged in a direction in which the radiation is emitted, the process comprising:

correcting a ratio of pixel values in a region, which corresponds to a soft tissue of a subject and is a corresponding region of radiographic images generated by the two radiation detectors irradiated with radiations having different energy levels, on the basis of correction data corresponding to a body thickness; and deriving at least one of bone density or bone mineral content of the subject on the basis of a difference between a ratio of pixel values in a region, which corresponds to a bone tissue of the subject and is a corresponding region of the radiographic images, and the corrected ratio of the pixel values.

* * * * *